(12) United States Patent
Kusters et al.

(10) Patent No.: US 11,389,578 B2
(45) Date of Patent: Jul. 19, 2022

(54) FLUID PROCESSING AND CIRCUIT ARRAY, SYSTEM AND APPARATUS

(71) Applicant: Fenwal, Inc., Lake Zurich, IL (US)

(72) Inventors: Benjamin E. Kusters, Pleasant Prairie, WI (US); Mark J. Brierton, Cary, IL (US)

(73) Assignee: Fenwal, Inc., Lake Zurich, IL (US)

( * ) Notice: Subject to any disclaimer, the term of this patent is extended or adjusted under 35 U.S.C. 154(b) by 400 days.

(21) Appl. No.: 15/768,140

(22) PCT Filed: Oct. 13, 2016

(86) PCT No.: PCT/US2016/056839
§ 371 (c)(1),
(2) Date: Apr. 13, 2018

(87) PCT Pub. No.: WO2017/066447
PCT Pub. Date: Apr. 20, 2017

(65) Prior Publication Data
US 2018/0311430 A1    Nov. 1, 2018

Related U.S. Application Data

(60) Provisional application No. 62/240,837, filed on Oct. 13, 2015.

(51) Int. Cl.
*A61M 1/26*  (2006.01)
*A61M 1/02*  (2006.01)
*A61M 1/36*  (2006.01)

(52) U.S. Cl.
CPC .......... *A61M 1/265* (2014.02); *A61M 1/0281* (2013.01); *A61M 1/3633* (2013.01); *A61M 2205/121* (2013.01); *A61M 2209/086* (2013.01)

(58) Field of Classification Search
None
See application file for complete search history.

(56) References Cited

U.S. PATENT DOCUMENTS 5,194,145 A    3/1993  Schoendorfer
5,868,696 A *  2/1999  Giesler ................. A61M 1/303
                                                604/6.12

(Continued)

FOREIGN PATENT DOCUMENTS

CN    103415334 A      11/2013
EP     0829265 B1 *    9/2001   .......... A61M 1/3672

(Continued)

OTHER PUBLICATIONS

Maini et al., Headstart Science (Class 6) 124 (2015). (Year: 2015).*

(Continued)

*Primary Examiner* — Magali P Slawski
*Assistant Examiner* — Brad Gordon
(74) *Attorney, Agent, or Firm* — Cook Alex Ltd.

(57) ABSTRACT

A fluid flow circuit assembly for a fluid processing device, comprising a housing having a plurality of openings, a separator disposed at least partially within the housing, and a plurality of flow paths communicating between an interior and an exterior of the housing via the plurality of openings, wherein the separator is disposed substantially at the center of the plurality of flow paths.

21 Claims, 11 Drawing Sheets

(56) References Cited

U.S. PATENT DOCUMENTS

| | | | |
|---|---|---|---|
| 6,471,855 B1* | 10/2002 | Odak | A61M 1/265 |
| | | | 210/512.1 |
| 7,874,409 B1* | 1/2011 | Lakhal | A45C 7/00 |
| | | | 190/103 |
| 2003/0229302 A1* | 12/2003 | Robinson | A61M 1/3489 |
| | | | 604/4.01 |
| 2005/0023207 A1 | 2/2005 | Kirker | |
| 2012/0230844 A1 | 9/2012 | Farrell et al. | |
| 2015/0166957 A1 | 6/2015 | Kusters et al. | |

FOREIGN PATENT DOCUMENTS

| | | |
|---|---|---|
| JP | 2002-527212 | 8/2002 |
| JP | 2015-527165 | 9/2015 |
| WO | 2000023140 A1 | 4/2000 |
| WO | 2014039086 A1 | 3/2014 |

OTHER PUBLICATIONS

International Preliminary Report on Patentability for application No. PCT/US16/56839, dated Apr. 19, 2017, 13 pages.

\* cited by examiner

FLUID PROCESSING AND CIRCUIT ARRAY, SYSTEM AND APPARATUS

CROSS-REFERENCE TO RELATED APPLICATIONS

This application is a national phase application of Int'l App. No. PCT/US16/56839 filed Oct. 13, 2016, which claims the benefit of U.S. Provisional Patent App. No. 62/240,837 filed Oct. 13, 2015, both of which are expressly incorporated herein by reference in their entireties.

FIELD OF THE DISCLOSURE

The present disclosure is directed to separation devices and methods of the type employing relatively rotating surfaces, at least one of which carries a membrane for filtering a component from fluid passed between the surfaces, and to a fluid flow circuit assembly incorporating such a separator.

BACKGROUND

Traditional blood collection may include manual collection of whole blood from healthy donors through blood drives, from donor visits to blood centers or hospitals and the like. In typical manual collection, whole blood is collected by simply flowing it, under the force of gravity and venous pressure, from the vein of the donor into a collection container. The amount of whole blood drawn is typically a "unit," which is about 450 ml.

Such a collection may employ a preassembled arrangement of tubing and containers or bags, including a flexible plastic primary container or bag for receiving a unit of whole blood from a donor and one or more "satellite" containers or bags. The blood may be first collected in the primary container, which may also contain an anticoagulant (typically containing sodium citrate, phosphate, and dextrose, often referred to as CPD). A preservative (often called an "additive solution" or AS, and commonly containing a saline, adenine, and glucose medium, which is referred to as SAG) may be included as part of a larger assembly of bags and tubes that are used in processing after the blood is collected.

After collection of a unit of whole blood, it is common practice in blood banking to transport the unit of whole blood, with connected tubing and containers, to a blood component processing laboratory, commonly referred to as a "back lab," for further processing. Further processing may entail manually loading the primary container and associated tubing and satellite containers onto a separator to separate the whole blood into components such as concentrated red cells and platelet-rich or platelet-poor plasma. These components may then be manually expressed from the primary container into other pre-connected satellite containers, and may again be separated to separate the platelets from plasma. Subsequently, the blood components may be leukoreduced by filtration for further processing or storage.

Another routine task performed by blood banks and transfusion centers is "cell washing." This may be performed to remove and/or replace the liquid medium (or a part thereof) in which the cells are suspended, to concentrate or further concentrate cells in a liquid medium, and/or to purify a cell suspension by the removal of unwanted cellular or other material.

Cell washing systems may involve centrifugation of a cell suspension, decanting of the supernatant, resuspension of concentrated cells in new media, and possible repetition of these steps until the cells of the suspension are provided at an adequately high or otherwise desirable concentration. Centrifugal separators used in the processing of blood and blood components may be used in such cell washing methods.

Another class of devices for separation includes a system based on the use of a membrane. Membrane-based systems have been used for plasmapheresis, that is separating plasma from whole blood. This type of device employs relatively rotating surfaces, at least one or which carries a porous membrane. The device may employ an outer stationary housing and an internal spinning rotor covered by a porous membrane.

Membrane-based systems may also be used for the collection of other blood components and for cell washing.

SUMMARY

According to an exemplary embodiment, the present disclosure is directed to a fluid flow circuit assembly for a fluid processing device, comprising a housing having a plurality of openings, a separator disposed at least partially within the housing, and a plurality of flow paths communicating between an interior and an exterior of the housing via the plurality of openings, wherein the separator is disposed substantially at the center of the plurality of flow paths.

According to an exemplary embodiment, the present disclosure is directed to a fluid flow circuit system for fluid processing, comprising a housing having a plurality of openings, and a separator disposed at least partially within the housing. The system also comprises a plurality of flow paths communicating between an interior and an exterior of the housing via the plurality of openings, wherein the plurality of flow paths are disposed along multiple planes. The system also comprises a loading platform of a fluid processing device, configured to engage at least one of the housing, separator, and plurality of flow paths, wherein the loading platform is capable of translational motion at least partially independent of a remainder of the fluid processing device.

According to an exemplary embodiment, the present disclosure is directed to a method of loading a fluid flow circuit assembly onto a fluid processing device, the method comprising providing a loading platform as part of a fluid processing device having at least one pump, the loading platform being capable of translational motion at least partially independent of the at least one pump of the fluid processing device. The method also comprises providing a fluid flow circuit assembly comprising a plurality of flow paths disposed along multiple planes, wherein the fluid flow circuit assembly is configured to engage the loading platform, and wherein at least one of the plurality of flow paths is configured to engage the at least one pump by the translational motion of the loading platform.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may improve organization of tubing, fluid paths, and components of a disposable kit into a compact enclosure to improve device loading and reduce device size.

Some embodiments may allow for fluid paths to run along multiple planes within an enclosure of a disposable kit for organization of components.

Some embodiments may decrease the area required for kit placement on a fluid processing device.

Some embodiments may eliminate the need for threading of tubing into position on a fluid processing device.

Figure 1:
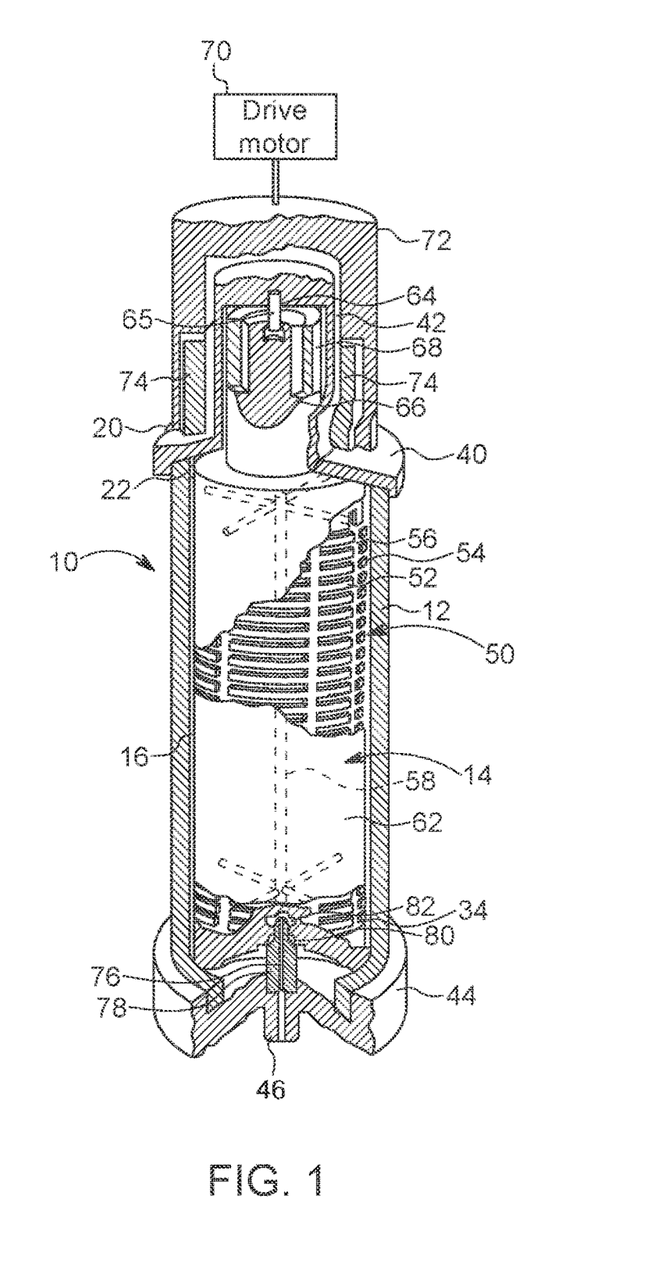
FIGS. 1 and 2 show a spinning membrane blood separation or fractionation system, according to an exemplary embodiment.
Figure 2:
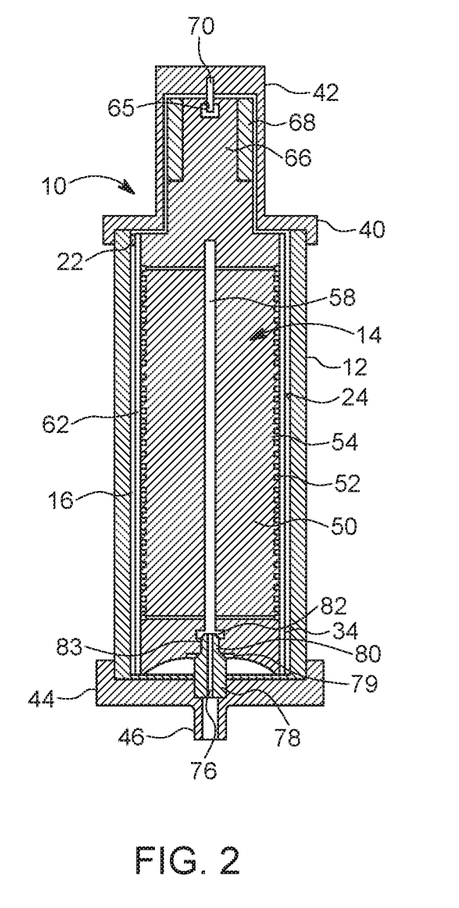

Turning to FIGS. 1 and 2, a spinning membrane blood separation system, generally designated 10, is shown. Such a system 10 may be used to extract plasma from whole blood obtained from an individual human donor. Detailed descriptions of spinning membrane separators may be found, for example, in U.S. Pat. No. 5,194,145 and Intl. App. Pub. No. WO2014039086, both of which are incorporated by reference herein in their entireties. The spinning membrane device 10 may form part of a disposable system including collection and return bags, bags of additives (e.g., saline, ACD), tubing, etc.

Figure 3:
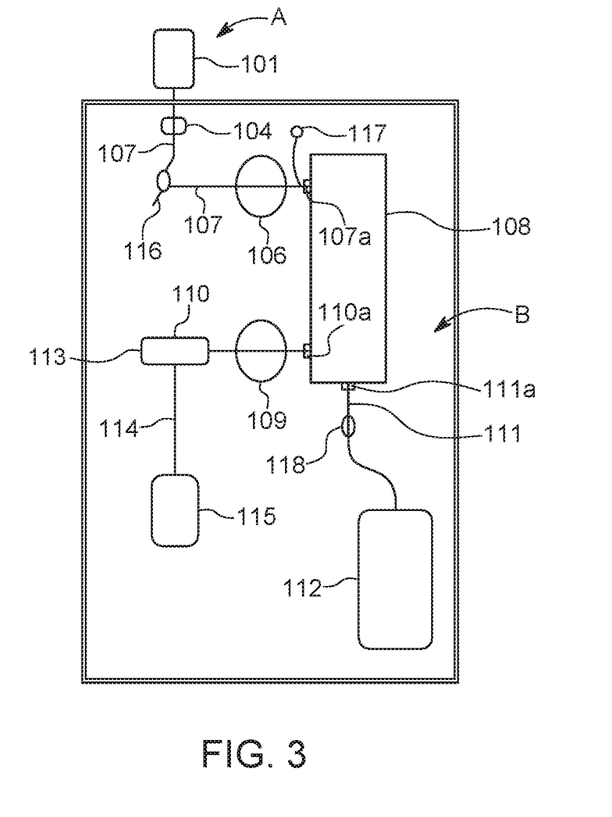
FIG. 3 is a schematic view of a disposable fluid flow circuit and a reusable durable controller configured to cooperate with and control flow through the fluid circuit, according to an exemplary embodiment.

Turning now to FIG. 3, a disposable fluid flow circuit or module A and a reusable durable controller or module B configured to cooperate with and control flow through the fluid circuit A are schematically illustrated. The disposable fluid circuit A as illustrated in FIG. 3 includes various components interconnected by flexible plastic tubing defining flow paths between the components. The circuit may be fully preassembled and pre-sterilized with the possible exception of the unit of whole blood container and the cell preservative container. More specifically, the illustrated disposable circuit in FIG. 3 may include whole blood container 101, blood component separator 108, plasma collection container 112, optional leukocyte reduction filter 113, and red cell collection container 115. While not illustrated in FIG. 3, the reusable module B may have hangers with associated weigh scales for supporting any or all of the containers 101, 112 and 115.

The whole blood collection container 101 may be any suitable container. Container 101 may be a flexible plastic pouch or bag in which approximately 450 ml of whole blood has been previously collected. Container 101 may be part of a separate system during collection and then joined to the rest of the fluid circuit A or actually part of the circuit A at the time of collection. At the time of collection, in accordance with customary procedure, the whole blood may be mixed with an anticoagulant located in the primary container 101 to prevent premature coagulation.

Flexible plastic tubing 107 is attached to the whole blood collection container 101, such as by a sterile connection device or other suitable attachment mechanism, and defines a whole blood fluid flow path between the whole blood container 101 and an inlet clamp 116. From the inlet clamp 116, the flow path extends through tubing 107 to an inlet port 107a in the separator 108.

As shown in FIG. 3, the separator housing has an outlet 110a that communicates with concentrated red cell flow path tubing 110 for withdrawing concentrated red cells from the separator. In addition, the housing includes an outlet 111a from the separator that communicates with plasma flow path tubing 111.

For reducing the number of leukocytes that may be present in the red cells, the disposable fluid flow circuit A may optionally include a leukocyte reduction filter 113, which may be of any suitable construction for removing leukocytes from concentrated red cells without unduly causing hemolysis of red cells or reducing the number of red cells in the collected product. The concentrated red cells may flow from the leukocyte reduction filter 113 through a continuation 114 of the concentrated red cell flow path into storage container 115 which may be of any suitable plastic material compatible with red cell storage.

The durable reusable controller or control module B may include an inlet clamp 116 which may be operated to control fluid from the whole blood container 101. For controlling flow of blood into the separator, the reusable module may include an inlet pump 106, which also may be of any suitable construction, and may be, for example, a peristaltic type pump which operates by progressive compression or squeezing of the tubing 107 forming the inlet flow path into the separator, a flexible diaphragm pump, or other suitable pump. A pressure sensor 117 may communicate with the inlet flow path between the pump 106 and the separator 108 to determine the inlet pumping pressure. The sensor may output to the control system to provide an alarm function in the event of an overpressure condition or an underpressure condition or both.

To control the flow rate of concentrated red cells from the separator 108, the reusable module may also include an outlet pump 109 that is associated with the outlet flow path 110, and may function in the manner similar to that described with respect to inlet pump 106. Pump 109 also may be of any suitable construction such as a peristaltic pump, a flexible diaphragm, or other suitable pumping structure. The plasma flow path 111 exiting the separator may be controlled by a volumetric flow rate through the plasma flow path tubing 111 that is the difference between the inlet volumetric flow rate from pump 106 and the outlet volumetric flow rate from pump 109. Reusable module B may, however, also include a clamp 118 for controlling flow of plasma through the plasma flow path tubing 111.

The disposable module A may also include a plasma collection container 112 in fluid communication with the plasma flow path 111 for receiving plasma separated by the separator 108. Because the plasma passes through a porous membrane in the separator 108, the plasma that is collected in container 112 may be largely cell free plasma and may be suitable for administration to patients, freezing for storage or subsequent processing.

Figure 4A:
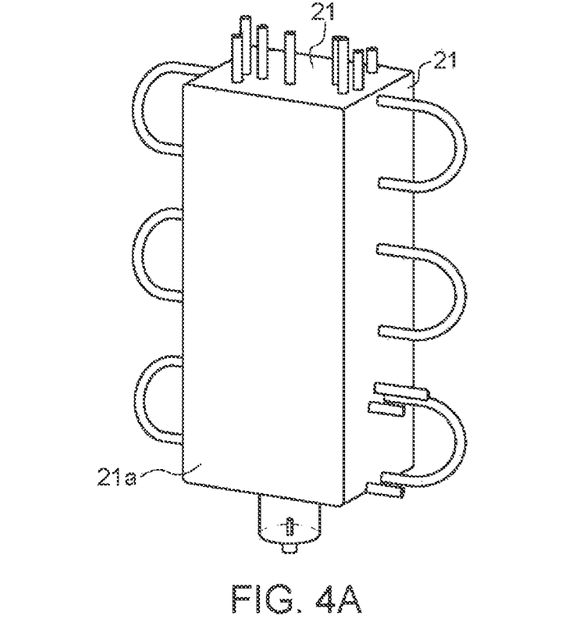
FIGS. 4A and 4B are front perspective views of the disposable fluid circuit of FIG. 3, according to an exemplary embodiment.
Figure 4B:
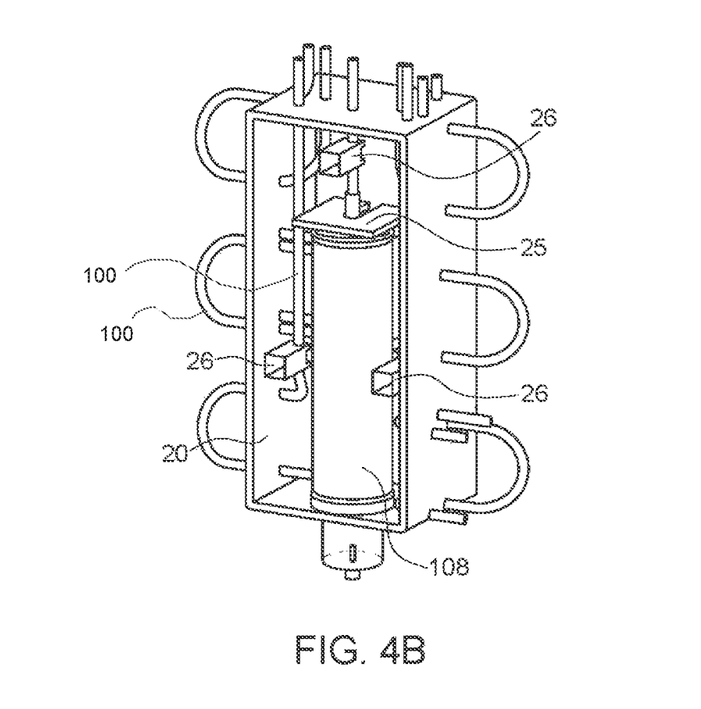

Turning to FIGS. 4A and 4B, front perspective views of one embodiment of the disposable module A is shown. This embodiment of disposable module A includes a plurality of walls 21 forming a housing 20, a separator 108, a separator support member 25, tubing guides 26, and flow paths 100 defining flow among components. Flow paths 100 are shown as formed with flexible tubing material, although any suitable material and/or method may be used (e.g., rigid material, molded channels, molded cassette). Regardless of the form of the flow paths, module A includes the separator and multiple fluid paths organized along multiple planes in a single component (e.g., entity). In other embodiments, module A may include the separator and multiple fluid paths organized substantially along a single plane in a single component. FIG. 4A shows wall 21a as opaque, and FIG. 4B shows wall 21a as transparent. The disposable module A is depicted in the general shape of a box in FIGS. 4A and 4B but may take on any shape (e.g., cylinder, ellipsoid, etc.).

Figure 5A:
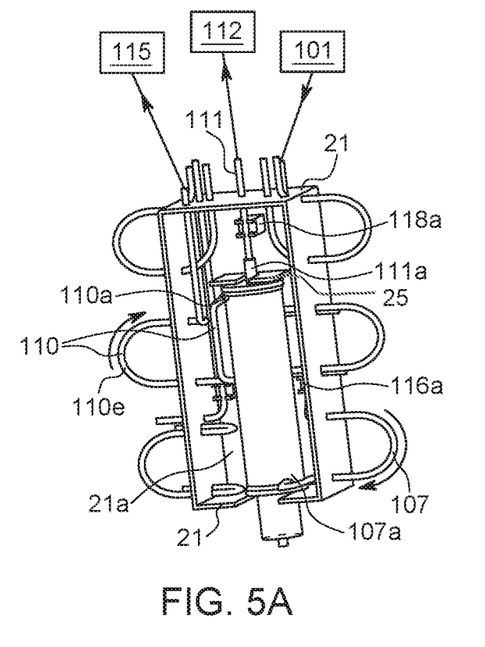
FIGS. 5A and 5B are back perspective views of the disposable fluid circuit of FIGS. 4A and 4B, according to an exemplary embodiment.
Figure 5B:
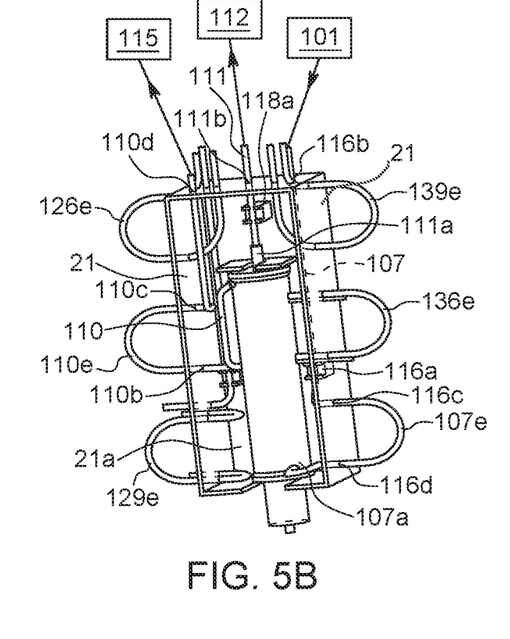

Turning to FIGS. 5A and 5B, back perspective views of the disposable module A are shown. The separator 108 may be supported generally within the walls 21 of disposable module A with the aid of the separator support member 25 and a bottom wall 21 of module A. The separator support member 25 may be affixed to a wall 21 of module A by a suitable method, such as injection molding. Similar to the embodiment of FIG. 3 above, the separator 108 of FIGS. 5A and 5B may have three ports 107a, 110a, and 111a, each connecting to respective flow paths 107, 110, and 111. Flow paths 107, 110, and 111 connect to their respective containers 101, 115, and 112.

It can be seen in FIG. 5B that tubing 107 is attached to the whole blood collection container 101, such as by a sterile connection device or other suitable attachment mechanism, and defines a whole blood fluid flow path between the whole blood container 101 and a tubing guide 116a. Flow path 107 may communicate between the exterior of module A (where container 101 is located) and the interior of module A (where separator 108 is located) via an opening 116b disposed at a top wall 21 of module A. Tubing guide 116a may serve to secure flow path 107 in place within module A by providing a friction fit with the tubing material and may be affixed to a wall 21 of module A by a suitable method, such as injection molding. From tubing guide 116a, flow path 107e may exit the interior of module A via opening 116c disposed at a side wall 21 of module A and may re-enter the interior of module A via another opening 116d disposed at a side wall 21. From opening 116d, flow path 107 extends to inlet port 107a of the separator 108 to complete the pathway between whole blood container 101 and the separator 108.

As shown in FIGS. 5A and 5B, outlet flow path 110 is attached to outlet port 110a of the separator 108 within the interior of module A and defines a concentrated red cell flow path between the separator 108 and red cell collection container 115. From outlet port 110a, flow path 110e may exit the interior of module A via opening 110b disposed at a side wall 21 of module A and may re-enter the interior of module A via another opening 110c disposed at a side wall 21. From opening 110c, flow path 110 extends to red cell collection container 115 located exterior to module A via opening 110d disposed at a top wall 21.

Figure 6:
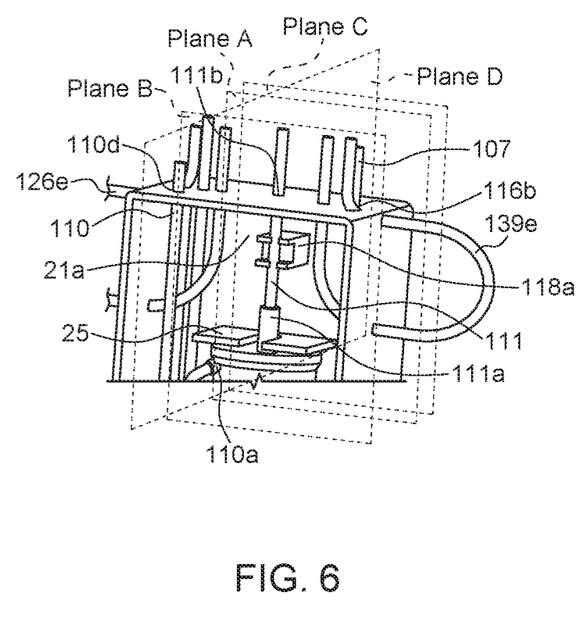
FIG. 6 is a perspective view of a top portion of the disposable fluid circuit of FIGS. 5A and 5B, according to an exemplary embodiment.

As shown in FIGS. 5A and 5B, outlet plasma flow path 111 is attached to outlet port 111a of the separator 108 within the interior of module A and defines a plasma flow path between the separator 108 and tubing guide 118a. Flow path 111 communicates between the exterior of module A (where plasma collection container 112 is located) and the interior of module A (where separator 108 is located) via an opening 111b disposed at a top wall 21 of module A. Tubing guide 118a may serve to secure flow path 111 in place within module A by providing a friction fit with the tubing material and may be affixed to a wall 21 of module A by a suitable method, such as injection molding. From tubing guide 118a, flow path 111 may exit the interior of module A via opening 111b from which flow path 111 extends to container 112 to complete the pathway between the separator 108 and plasma collection container 112. FIG. 6 depicts a close-up view of a top portion of module A.

In addition to flow paths 107, 110, and 111 that connect to the separator 108, tubing loops 126e, 129e, 136e, and 139e are depicted in the embodiment of FIGS. 5A and 5B. Tubing loops 126e, 129e, 136e, 139e may be connected to other fluid flow paths as required by the fluid processing procedure. Examples of fluids often used in blood processing procedures include saline, anticoagulant, additive solution, cell preservative solution. In the event that one or more of these fluids are utilized in the procedure, corresponding tubing loops 126e, 129e, 136e, and/or 139e may be connected to one or more containers containing these fluids. Tubing loops 126e, 129e, 136e, and/or 139e may also be connected to a donor during the return and/or draw phase of blood processing.

The fluid paths organized by module A may be stacked and/or disposed along multiple planes. For example, referring to FIGS. 5B and 6, tubing loops 136e and 110e may be located on one plane (e.g., Plane A), while flow path 110 exiting through opening 110d may be located on a different plane (e.g., Plane B). Flow path 110 exiting through opening 110d is shown in FIG. 5B to be positioned farther from the front 21a of module A (back of FIG. 5B) than are tubing loops 136e and 110e. In another example, referring to FIG. 6, tubing loops 126e and 139e may be located on one plane (e.g., Plane A), while flow path 111 exiting through opening 111b may be located on a different plane (e.g., Plane C). Tubing loops 126e and 139e in FIG. 6 are positioned farther from the front 21a of module A (back of FIG. 6) than is flow path 111 exiting through opening 111b. Flow paths 110 and 111 may also be positioned along different planes, and in the embodiment in FIG. 6, flow path 110 is disposed along a plane that is farther from the front 21a of module A, while flow path 111 is disposed along a plane that is closer to the front 21a of module A (back of FIG. 6) relative to the plane of flow path 110. In yet another example, fluid paths may be positioned along different planes that are perpendicular or transverse to each other. Referring to FIGS. 5B and 6, the plane (e.g., Plane A) on which tubing loops 136e and 110e are located is, according to one embodiment; transverse or nearly perpendicular to the plane (e.g.; Plane D) on which flow path 111 emanating from outlet port 111a and flow path 110 emanating from outlet port 110a are located. In other embodiments, the separator, housing, and fluid paths may be configured such that all fluid paths are positioned along a single plane (e.g., Plane A). In some embodiments, it may be beneficial for the separator and fluid paths to be disposed within the housing 20 in an integrative fashion as to form a substantially integral entity. For example, FIGS. 5A and 5B show separator 108 as surrounded by various flow paths (e.g., 107, 110, 111) with the separator 108 disposed substantially at the center of the integral entity.

Figure 7:
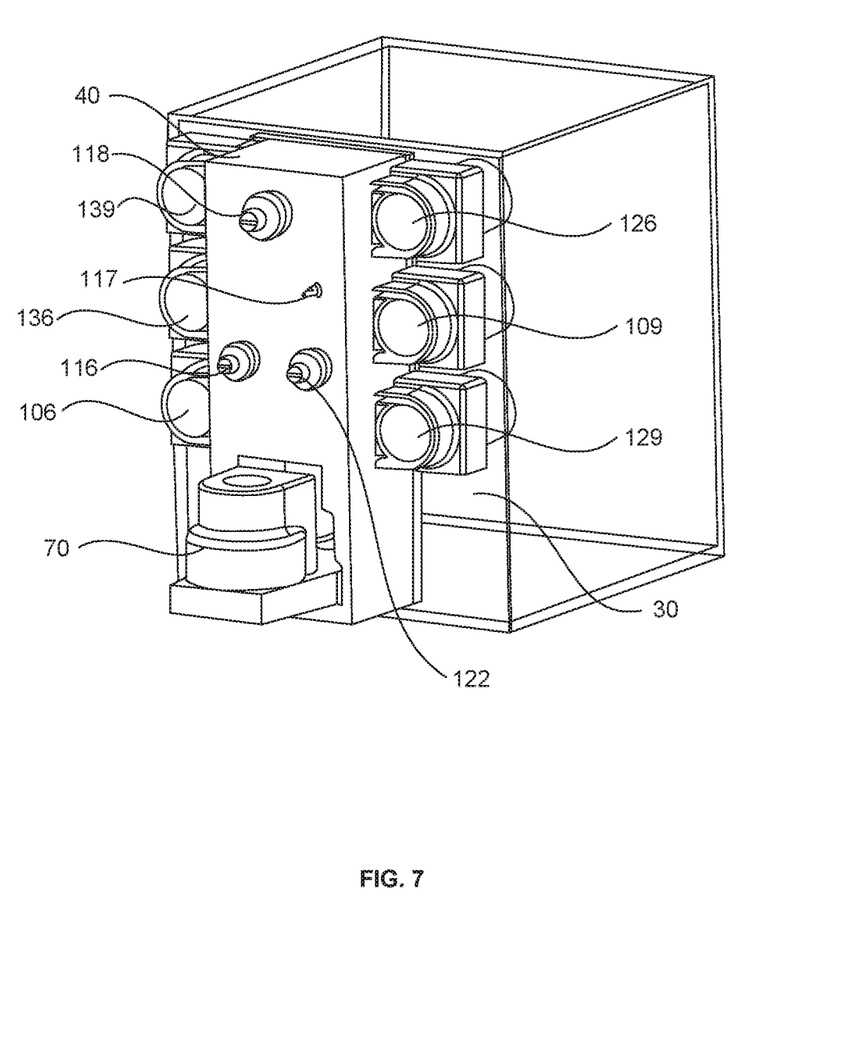
FIG. 7 is a perspective view of the reusable durable controller of FIG. 3, according to an exemplary embodiment.

Turning to FIG. 7, one embodiment of reusable durable controller or module B is shown. The embodiment of module B in FIG. 7 includes three clamps 116, 118, 122, six pumps 106, 109, 126, 129, 136, 139, and a pressure sensor 117. However, device configuration and components of module B (e.g., number of pumps, clamps, sensors) may vary based on implementation platforms and fluid processing goals. Based on different embodiments of module B, the configuration of module A may correspondingly change to be compatible with module B.

Referring to FIG. 7, pumps 106, 109, 126, 129, 136, 139 are shown mounted to a stationary body 30. Clamps 116, 118, 122 and pressure sensor 117 are mounted to a loading platform 40. A separator drive motor 70 may also be mounted to the loading platform 40. Loading platform 40, along with the components mounted to it, may be capable of translational motion independent of pumps 106, 109, 126, 129, 136, 139 and stationary body 30.

Figure 8:
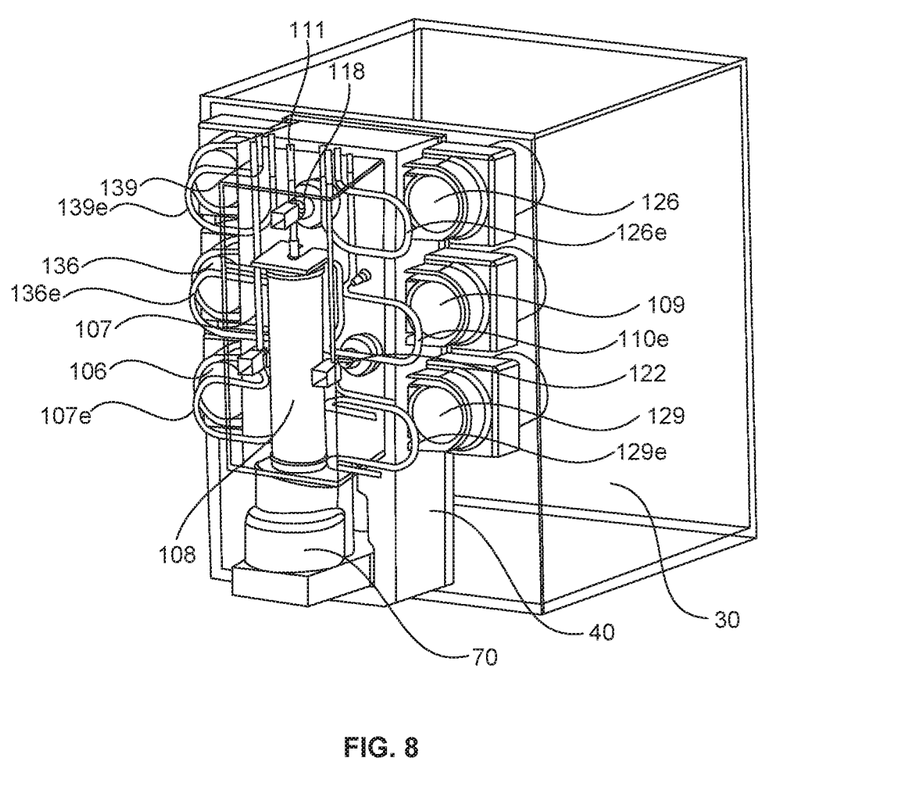
FIG. 8 is a perspective view of a loaded state of the disposable module of FIGS. 4A and 4B onto a loading platform of the reusable durable controller of FIG. 3, according to an exemplary embodiment.

FIG. 8 depicts the loaded state of disposable module A onto the loading platform 40 of reusable durable module B. The separator 108 may be mounted onto drive motor 70 of loading platform 40 by a user. When separator 108 and drive motor 70 are engaged, flow paths 107 and 111 may automatically be placed adjacent to corresponding clamps 116 and 118, respectively, by virtue of the configuration of module A. Likewise, tubing loops 107e and 110e may be placed adjacent to corresponding pumps 106 and 109, respectively. In an embodiment in which tubing loops 126e, 129e, 136e, and/or 139e are utilized, for example, for saline, anticoagulant, additive solution, cell preservative solution, draw line from a donor, and/or return to a donor, the tubing loops may be placed adjacent to corresponding pumps 126, 129, 136, and/or 139. Manual user loading and threading of these components onto hardware may thereby not be required. At this initial loaded state, the loading platform 40 is extended outward away from the stationary body 30 and from pumps 106, 109, 126, 129, 136, 139.

Figure 10:
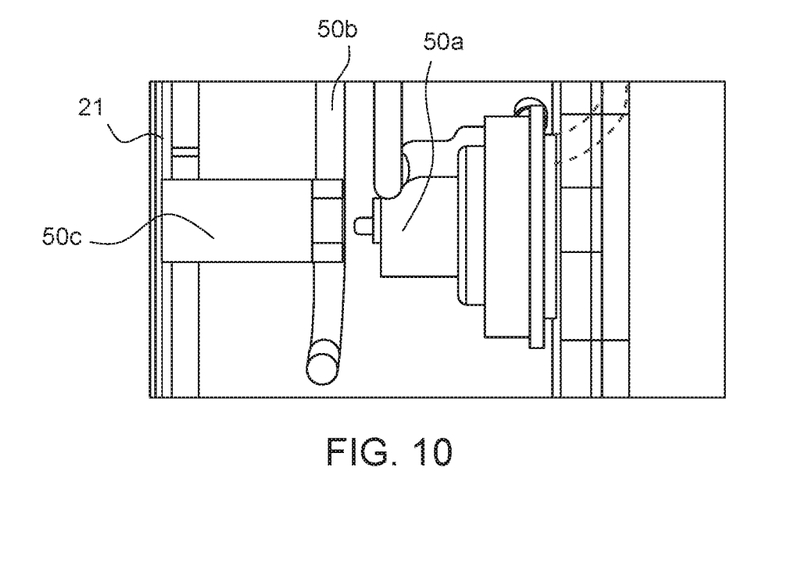
FIG. 10 is a perspective side view of a representative flow path prior to engagement with a corresponding representative clamp, according to an exemplary embodiment.
Figure 11:
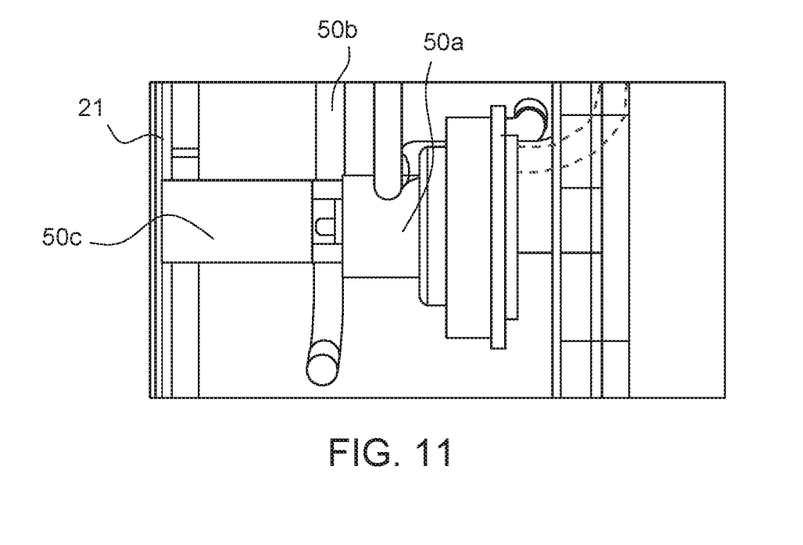
FIG. 11 is a perspective side view of the flow path of FIG. 10 during engagement with the clamp of FIG. 10, according to an exemplary embodiment.

According to an exemplary embodiment, FIG. 10 provides a perspective side view of a representative flow path 50b prior to engagement with a corresponding representative clamp 50a. According to an exemplary embodiment, FIG. 11 provides a perspective side view of flow path 50b during engagement with clamp 50a. Flow path 50b may be representative of any flow path within module A that engages with a clamp 50a of module B. Tubing guide 50c may secure flow path 50b in place within module A by gripping (e.g., friction fit) the flow path material. Tubing guide 50c may be affixed to a wall 21 of module A. Tubing guide 50c may also function as a backstop against which flow path 50b is held while clamp 50a occludes flow path 50b, as shown in FIG. 11.

Figure 9:
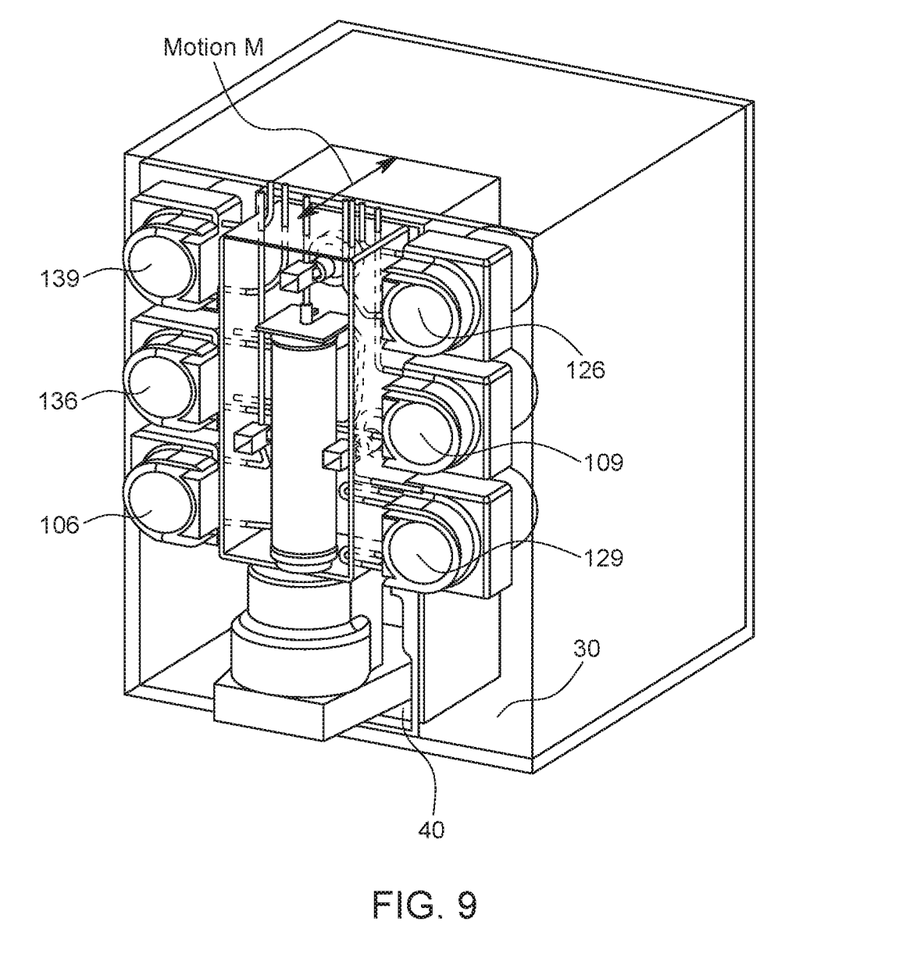
FIG. 9 is a perspective view of a loaded state of the disposable module of FIGS. 4A and 4B onto pumps mounted to a stationary body of the reusable durable controller of FIG. 3; according to an exemplary embodiment.

According to an exemplary embodiment, FIG. 9 depicts the loaded state of disposable module A onto pumps 106, 109, 126, 129, 136, 139 that are mounted to the stationary body 30. At this fully loaded state, the loading platform 40 is extended inwards toward the stationary body 30 and toward pumps 106, 109, 126, 129, 136, 139. The loading platform 40 may undergo translational motion to automatically load module A onto the pumps. Platform 40 may be at least partially disposed within the stationary body 30 in the fully loaded state. By configuring module A to correspond with module B by three-dimensional organization of fluid paths, the fluid paths may be correctly loaded onto their corresponding pumps by translational motion of the loading platform 40 alone. When a fluid processing procedure is complete, loading platform 40 may move back out of stationary body 30 to unload the pumps. The translational motion of loading platform 40 is depicted in FIG. 9 as motion M.

The embodiments described may enable a fluid processing device to take on more compact dimensions with smaller surface area. Traditional methods of loading a disposable kit may require a user to thread tubing into clamps, pumps, pressure sensor, and holders/guides. Also, the kit and its fluid paths were typically mounted across front and side (2-D) planes of the durable hardware, i.e., fluid paths were two-dimensional, unstacked, and limited to one plane. Consequently, the same dimensions may not be able to accommodate the increasing amounts of surface area required as the amount of components increased with increasing complexity of procedures.

Figure 12:
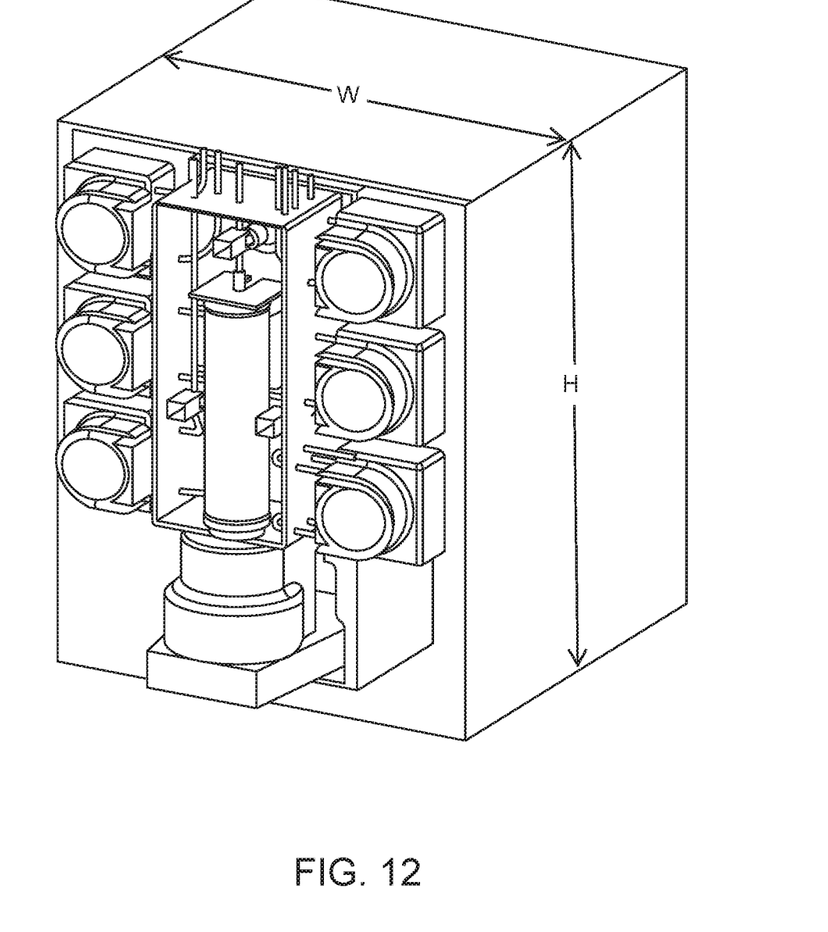
FIG. 12 is a perspective view of the reusable durable controller of FIG. 3, according to an exemplary embodiment.

FIG. 12 depicts module B having smaller dimensions by virtue of the described embodiments. The stationary body 30 may have a height H as low as 15 inches and a width W as low as 12 inches. In contrast, traditional fluid processing hardware have been known to have height and width values of approximately 18 inches each.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A fluid flow circuit system for fluid processing, comprising:
    a disposable module including:
        a housing having a plurality of openings;
        a separator disposed at least partially within the housing; and
        a plurality of flow paths communicating between an interior and an exterior of the housing via the plurality of openings, wherein the plurality of flow paths are disposed along multiple planes; and
    a durable module including a loading platform and a loading platform drive motor, wherein
        the loading platform is configured to engage at least one of the housing, separator, and plurality of flow paths, and
        the loading platform drive motor is configured to cause the loading platform to undergo translational motion at least partially independent of a remainder of the durable module so as to automatically move the disposable module into and out of association with the remainder of the durable module.

2. The fluid flow circuit system of claim 1, wherein the separator is disposed substantially at the center of the plurality of flow paths.

3. The fluid flow circuit system of claim 1, wherein the housing and the plurality of flow paths are in a form of a molded cassette.

4. The fluid flow circuit system of claim 1, wherein the plurality of flow paths comprise at least a first flow path in a first plane and at least a second flow path in a second plane.

5. The fluid flow circuit system of claim 4, wherein the first plane and the second plane are disposed parallel to each other.

6. The fluid flow circuit system of claim 5, further comprising a third flow path in a third plane, wherein the third plane is disposed transverse to the first and second planes.

7. The fluid flow circuit system of claim 1, wherein a separator drive motor is disposed on the loading platform and configured to engage the separator.

8. The fluid flow circuit system of claim 7, wherein the plurality of flow paths are disposed adjacent to corresponding clamps of the loading platform and/or corresponding pumps of the remainder of the durable module when the separator and the separator drive motor are engaged.

9. The fluid flow circuit system of claim 1, wherein said remainder of the durable module includes at least one pump from which the loading platform is configured to move independently.

10. The fluid flow circuit system of claim 1, wherein
a surface of said remainder of the durable module defines a cavity, and
at least a portion of the loading platform is configured to move into the cavity by translational motion in a first direction so as to associate the disposable module to said remainder of the durable module and to move out of the cavity by translational motion in an opposite second direction so as to dissociate the disposable module from said remainder of the durable module.

11. A method of loading a disposable module including a housing having a plurality of openings, a separator disposed at least partially within the housing, and a plurality of flow paths communicating between an interior and an exterior of the housing via the plurality of openings and disposed along multiple planes onto a durable module and unloading the disposable module from the durable module, the method comprising:
mounting the disposable module onto a loading platform of the durable module,
actuating a loading platform drive motor of the durable module to translationally move the loading platform with respect to a remainder of the durable module so as to automatically cause at least one of the plurality of flow paths to engage at least one pump of the durable module, and
actuating the loading platform drive motor of the durable module to translationally move the loading platform with respect to the remainder of the durable module so as to automatically cause said at least one of the plurality of flow paths to disengage said at least one pump.

12. The method of claim 11, wherein the plurality of flow paths comprise at least a first flow path in a first plane and at least a second flow path in a second plane.

13. The method of claim 12, wherein the first plane and the second plane are disposed parallel to each other.

14. The method of claim 13, further comprising a third flow path in a third plane, wherein the third plane is disposed transverse to the first and second planes.

15. The method of claim 11, wherein at least one flow path is secured in place by a tubing guide affixed to a wall of the housing of the disposable module.

16. The method of claim 11, wherein a separator drive motor is disposed on the loading platform and configured to engage the separator of the disposable module.

17. The method of claim 16, wherein the plurality of flow paths are disposed adjacent to corresponding clamps of the loading platform and/or corresponding pumps of the durable module when the separator and the separator drive motor are engaged.

18. The method of claim 11, wherein the separator is disposed substantially at the center of the plurality of flow paths.

19. The method of claim 11, wherein the housing and the plurality of flow paths are in a form of a molded cassette.

20. A fluid flow circuit system for fluid processing, comprising:
a disposable module including:
a housing having a plurality of openings;
a separator disposed at least partially within the housing; and
a plurality of flow paths communicating between an interior and an exterior of the housing via the plurality of openings, wherein the plurality of flow paths are disposed along multiple planes; and
a durable module including:
at least one pump;
a loading platform; and
a loading platform drive motor, wherein
the loading platform is configured to engage at least one of the housing, separator, and plurality of flow paths, and
the loading platform drive motor is configured to cause the loading platform to undergo translational motion at least partially independent of a remainder of the durable module so as to automatically move at least a portion of the disposable module into and out of engagement with the at least one pump.

21. A fluid flow circuit system for fluid processing, comprising:
a disposable module including:
a housing having a plurality of openings,
a separator disposed at least partially within the housing, and
a plurality of flow paths communicating between an interior and an exterior of the housing via the plurality of openings, wherein the plurality of flow paths are disposed along multiple planes and include a plurality of tubing loops; and
a durable module including a loading platform and one or more pumps, wherein
the loading platform is configured to engage at least one of the housing, separator, and plurality of flow paths,
the loading platform is configured to undergo translational motion at least partially independent of a remainder of the durable module so as to move the entire housing of the disposable module with respect to the remainder of the durable module, and
the plurality of tubing loops are configured to engage the one or more pumps via the translational motion of the loading platform.

* * * * *